(12) United States Patent
Sullivan et al.

(10) Patent No.: US 7,713,752 B2
(45) Date of Patent: May 11, 2010

(54) MAGNETIC BEAD AGGLOMERATOR FOR AUTOMATED ELISA PROCESS

(75) Inventors: Brian M. Sullivan, Redondo Beach, CA (US); Denes L. Zsolnay, Rolling Hills Estates, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 1680 days.

(21) Appl. No.: 10/374,270

(22) Filed: Feb. 25, 2003

(65) Prior Publication Data
US 2004/0166547 A1      Aug. 26, 2004

(51) Int. Cl.
*G01N 33/553*    (2006.01)
*B05D 7/00*     (2006.01)
(52) U.S. Cl. ............... 436/526; 436/435; 436/518; 210/42; 210/222; 210/695; 427/212
(58) Field of Classification Search ......... 436/426, 436/435, 518; 210/222, 42, 695; 427/212
See application file for complete search history.

(56) References Cited

U.S. PATENT DOCUMENTS

| | | | | |
|---|---|---|---|---|
| 3,985,649 A | * | 10/1976 | Eddelman | 210/695 |
| 4,116,829 A | * | 9/1978 | Clark et al. | 210/695 |
| 5,110,624 A | * | 5/1992 | Noble et al. | 427/212 |
| 5,158,748 A | * | 10/1992 | Obi et al. | 422/100 |
| 5,164,598 A | * | 11/1992 | Hillman et al. | 250/341.3 |
| 5,565,365 A | * | 10/1996 | Glass | 436/526 |
| 2001/0007312 A1 | * | 7/2001 | Siddiqi | 210/695 |

* cited by examiner

*Primary Examiner*—Mark L Shibuya
*Assistant Examiner*—Pensee T Do
(74) *Attorney, Agent, or Firm*—Tarolli, Sundheim, Covell & Tummino LLP

(57) ABSTRACT

Mixing of a sample containing a suspect bioagent or antigen with 1° recognition molecule coated magnetic beads in the preliminary stage of an enzyme linked immunoassay ("ELISA") procedure is emulated by first inserting the coated magnetic beads into a non-magnetic confinement region, generating a magnetic field B along the axis of said non-magnetic confinement region to agglomerate the coated magnetic beads into a porous mass; then percolating or otherwise forcing the sample solution through said porous mass; and withdrawing the magnetic field to de-agglomerate said coated magnetic beads. In seeping or otherwise flowing through the magnetic beads the molecules of the sample link to respective magnetic beads that are coated with recognition molecules.

3 Claims, 3 Drawing Sheets

MAGNETIC BEAD AGGLOMERATOR FOR AUTOMATED ELISA PROCESS

REFERENCE TO PRIOR APPLICATIONS

Reference is made to U.S. application Ser. No. 09/837,946, filed Apr. 19, 2001, entitled "Automated Computer Controlled Reporter Device for Conducting Immunoassay and Molecular Biology Procedures."

FIELD OF THE INVENTION

This invention relates to automated reporter devices for conducting immunoassay and molecular biology procedures on a test sample to detect bioagents (and/or nucleic acids), and, more particularly, to an improved apparatus and process for applying the sample to recognition molecule coated magnetic beads, such as antibody coated magnetic beads, used in the foregoing automated reporter device.

BACKGROUND

One known test procedure or process for detection of a specific bioagent that is applicable to a variety of fields, such as biotechnology, environmental protection and public health, is the enzyme linked immunoassay (hereafter referred to as "ELISA"). The ELISA process constitutes an identification process that uses molecular interactions to uniquely identify target substances. A basic definition of ELISA is a quantitative in vitro test for an antibody or antigen (e.g., a bioagent) in which the test material is adsorbed on a surface and exposed to a complex of an enzyme linked to an antibody specific for the substance being tested for with a positive result indicated by a treatment yielding a color in proportion to the amount of antigen or antibody in the test material. The basic ELISA procedure is described more specifically, for one, in a book entitled Methods in Molecular Biology Vol. 42, John R. Crowther, Humana Press, 1995.

The "antibody specific for the substance being tested for" in the foregoing definition constitutes one type of recognition molecule, a molecule that is capable of binding to either reactant or product molecules in a structure-restricted manner. That is, the recognition molecule binds to a specific three-dimensional structure of a molecule or to a two-dimensional surface that is electrically charged and/or hydrophobic in a specific surface pattern. It may also be recognized that ELISA-like approaches using other recognition molecules can also be used, such as aptamers, DNA, RNA and molecular imprint polymers.

More recently, the foregoing definition for ELISA has been expanded beyond the colormetric approach, in which color and color intensity is used as the reporter or indicia of the antigen or antibody, to include a voltametric or amperiometric approach to detection and assay, in which the rate of change of voltage or current conductivity is proportional to the amount of antigen or antibody contained in the test material. Patent Cooperation Treaty application PCT/US98/16714, filed Aug. 12, 1998 (International Publication No. WO 99/07870), entitled "Electrochemical Reporter System for Detecting Analytical Immunoassay and Molecular Biology Procedures" (hereafter the "16714 PCT application"), claiming priority of U.S. patent application Ser. Nos. 09/105,538 and 09/105,539"), to which the reader may refer, describes both a colormetric and an electrochemical reporter system for detecting and quantifying enzymes and other bioagents in analytical and clinical applications. The electrochemical reporter system of the 16714 PCT application employs a sensor for detecting voltametric and/or amperiometric signals that are produced in proportion to the concentration of organic (or inorganic) reporter molecules by redox (e.g. reduction-oxidation) recycling at the sensor.

In brief, in the ELISA test, the suspect bioagent is initially placed in a water-based buffer, such as a phosphate buffered saline solution, to form a sample solution. That sample solution is mixed with a quantity of particles, beads, the surface of which is coated with a recognition molecule for the suspect bioagent (also sometimes referred to as a receptor molecule). The particular recognition molecule used to coat the beads is known to bind to the bioagent of interest and is a primary recognition molecule (antibody) or "1° Ab." That is, the recognition molecule coating exhibits a chemical "stickiness" that is selective to specific bioagents.

Any bioagent that is present in the sample solution binds with a non-covalent bond to a respective recognition molecule and thereby becomes attached to a respective one of the beads in the mixture-solution. If the sample solution does not contain a bioagent or if the bioagent that is present in the solution is not one that binds to the selected recognition molecule, then the recognition molecule remains unbound. Further processing of the ELISA process then shows nothing.

Assuming the suspect bioagent is present in the sample, the bioagent bonds to the coating on the beads. The solution then contains a quantity of bioagent molecules bound respectively to a quantity of coated beads. The mixture is optionally washed, as example, in a phosphate-buffered saline, and a second recognition molecule, more specifically, a recognition molecule and enzyme linked combination, is then added to the mixture. The second recognition is also one that is known to bind to the suspect bioagent. The second recognition molecule may either be one that is monoclonal, e.g. one that binds to only one specific molecule, or polyclonal, e.g. a mixture of different antibodies each of which shares the characteristic of bonding to the target bioagent. The enzyme is covalently bound to the second recognition molecule and forms a complex that is referred to as a secondary recognition molecule-enzyme conjugate or "2° Ab-enz." As known by those skilled in the art, an enzyme is a "molecular scissors", a protein that catalyzes a biological reaction, a reaction that does not occur appreciably in the absence of the enzyme. The enzyme is selected to allow the subsequent production of an electrochemically active reporter.

The 2° Ab-enz binds to the exposed surface of the immobilized bioagent to form a "recognition molecule sandwich" with the bioagent forming the middle layer of that sandwich. The recognition molecule sandwich coated beads are washed again to wash away any excess 2° Ab-enz in the solution that remains unbound.

The beads and the attached recognition molecule sandwich, the 1° Ab/bioagent/2° Ab-enz complex, in the solution are placed over the exposed surface of the redox recycling sensor. The substrate of the foregoing enzyme is added to the solution and the substrate is cleaved by the enzyme to produce an electrochemically active reporter. The substrate of the enzyme, referred to as PAP-GP, is any substance that reacts with an enzyme to modify the substrate. The effect of the enzyme is to separate, cut, the PAP, a para-amino phenol, the electrochemically active reporter, from the GP, an electrochemically inactive substance.

The foregoing chemical reaction is concentrated at the surface of the sensor. The rate of production of the foregoing reporter (PAP) is proportional to the initial concentration of bioagent. The reporter reacts at the surface of the sensor, producing an electrical current through the sensor that varies with time and is proportional to the concentration of the bioagent, referred to as redox recycling. The occurrence of the electric current constitutes a positive indication of the presence of the suspect bioagent in the sample. Analysis of the electric currents produced over an interval of time and comparison of the values of that electric current with existing laboratory standards of known bioagents allows quantification of the concentration of bioagent present in the initial sample.

Recognizing that need, the present inventors, together with other co-inventors, created an automated test procedure and apparatus, which is described in U.S. patent application Ser. No. 09/837,946, filed Apr. 19, 2001, entitled Automated Computer Controlled Reporter Device for Conducting Immunoassay and Molecular Biology Procedures (hereafter the "946 application"), assigned to the assignee of the present application, the content of which is incorporated herein by reference. The apparatus of the '946 application, hereafter referred to as the automated ELISA system, provides a user friendly stand-alone portable automated system that is able to automatically perform an ELISA test. The automated ELISA system contains a number of solutions in respective reservoirs and pumps that are controlled by a programmed computer. That automated unit may be operated by persons who are not biologists and who require minimal training to operate the unit.

The foregoing automated ELISA system also employs coated beads of magnetic material and a magnetic positioning device to manipulate and position the coated magnetic beads under control of the computer, such as during the washing steps of the ELISA process, and in positioning the beads at the sensor during redox recycling. The automated ELISA system of the '946 application provides a solution that permits wide dispersal of testing units among the general population that takes into account the lesser skills of the prospective operators for those units.

In a first step of the assay procedure the sample solution, containing the sample that is to be tested for the presence of a specific bioagent, is placed in a container (or equivalent vessel) containing the 1° recognition molecule coated magnetic beads, and the contents of the container is mixed together to ensure that the respective parts, that is, molecules of the sample contacts the coating of a respective bead. If the sample is of the specific bioagent, then the respective parts of the sample link or, as variously termed, stick to the recognition molecule coating of a respective bead. In the automated ELISA apparatus of the '946 application, the sample solution and the coated beads are pumped into the common container by electrical pumps controlled by a programmed computer. Although the injection of the two ingredients into a single container was originally thought to sufficiently mix the two ingredients, current thinking is that mixing with greater thoroughness provides a more accurate assay and a better result.

One result of the process is to determine how much of the bioagent is in the solution; that is, the concentration. The purpose of mixing the solution of sample and coating beads is to ensure that every portion of the sample has an opportunity to strike the coating of a bead in order to attach or link as much of the sample as possible. In practice, the volume of the sample and bead solution is small and the container, which may be a length of pipette tubing, is also small. A known practical way to mix the ingredients of the solution is to create turbulence by repeatedly pumping the foregoing solution out of the container and then pumping that solution back into the container or to recirculate that solution. It is found that the foregoing approach to mixing is not as efficient as desired. Not only must additional pumps and/or valves and plumbing be included in the automated system or the pumps and/or valves that are included in the automated system must be adapted to that task, which increases the complexity of that system, but, more importantly, due to the inefficiency of that mixing process, considerable mixing time is required to ensure that molecules of the sample have the opportunity to link to an available coated bead, an effect here described as thorough mixing.

Accordingly, a principal purpose of the present invention is to bring the molecules of the sample into close association with the recognition molecule coated magnetic beads in the automated system in a shorter period of time and with greater efficiency than previously carried out.

An additional purpose of the invention is to increase the effectiveness of the automated computer controlled reporter device for conducting immunoassay and molecular biology procedures disclosed in the '946 application.

SUMMARY OF THE INVENTION

In accordance with the foregoing purpose, a sample in solution that contains a suspect bioagent or antigen is linked to recognition molecule coated magnetic beads by first inserting the coated magnetic beads into a non-magnetic confinement region, generating a static magnetic field along the axis of said non-magnetic confinement region to agglomerate the coated magnetic beads into a porous mass that essentially fills the region; and then percolating or otherwise flowing the sample solution through that porous mass. In seeping or flowing through the magnetic beads the molecules of the sample solution are directly exposed to and stick to respective available coated magnetic beads, thereby at least emulating the thorough mixing earlier described. Thereafter the magnetic field is withdrawn to de-agglomerate the coated magnetic beads, readying the coated beads for further treatment in an ELISA process.

The foregoing and additional objects and advantages of the invention, together with the structure characteristic thereof, which were only briefly summarized in the foregoing passages, will become more apparent to those skilled in the art upon reading the detailed description of a preferred embodiment of the invention, which follows in this specification, taken together with the illustrations thereof presented in the accompanying drawings.

DETAILED DESCRIPTION OF THE PREFERRED EMBODIMENTS

Figure 1:
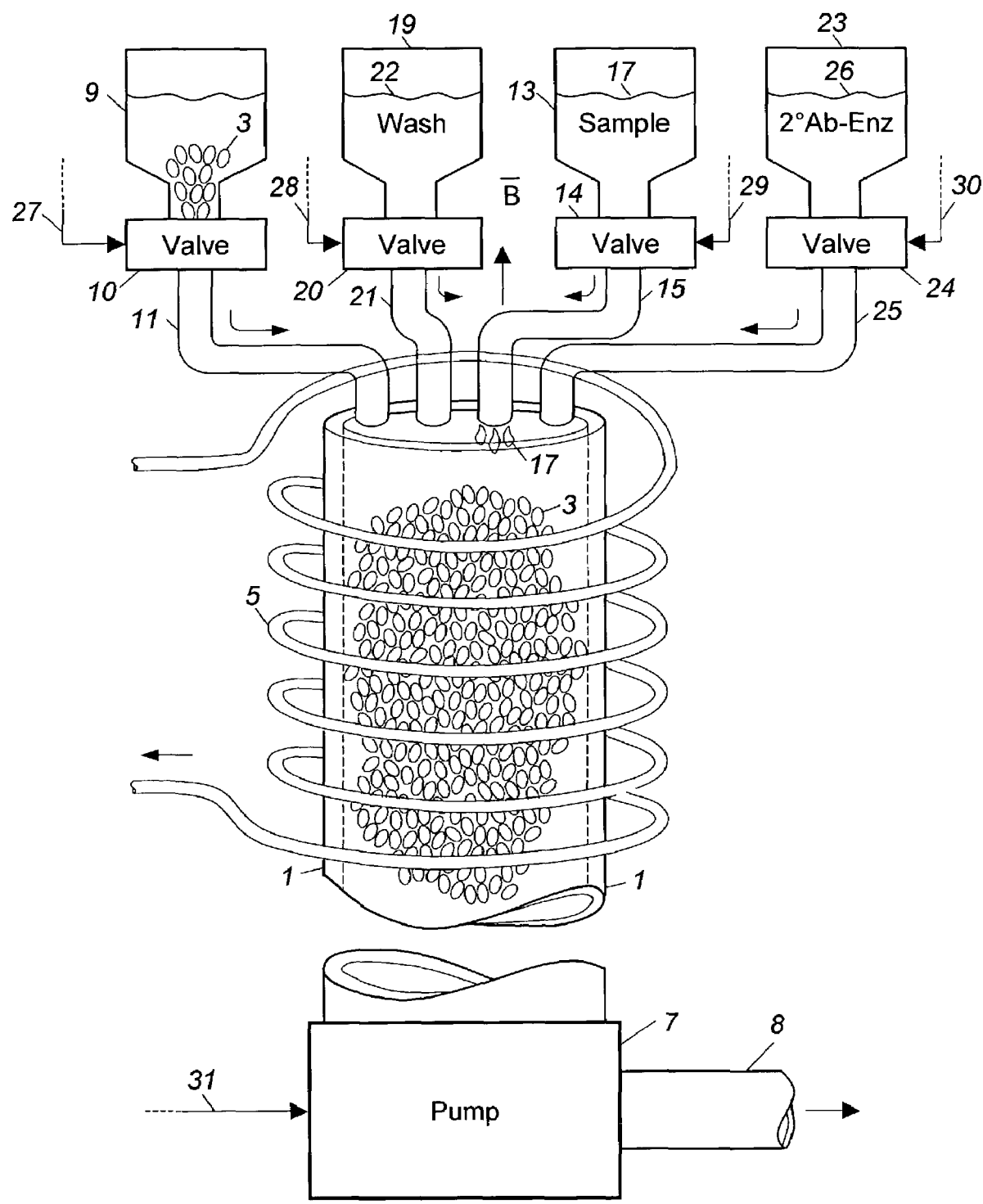
FIG. 1 illustrates an embodiment of the invention.

FIG. 1, to which reference is made, pictorially illustrates a preferred embodiment of the novel "mixer" apparatus in which the sample of suspect bioagent is mixed with, intermingled with or bathes the antibody coated magnetic beads. The apparatus includes a length of pipette or glass tube 1 that serves as a non-magnetic "reaction" chamber or confinement region for the coated magnetic beads 3, which are shown disposed inside the hollow glass cylinder, and an electric coil 5 that defines an air-core solenoid. The relationship between the magnetic beads, the glass tube and the electric coil that is illustrated in the pictorial in which coated magnetic beads 3 form an agglomerate is the relationship obtained when DC current flows through electric coil 5. That DC current is applied to the coil, following the introduction of the coated magnetic beads 3 within tube 1, later herein described in greater detail. Electric coil 5 is formed of multiple turns of electrical wire, suitably insulated wire, wound about the axis of glass tube 1, that extends over a predetermined axial length of the glass tube 1 to form a helix.

The inlet of an electric pump 7 connects to the bottom end of tube 1 and in this embodiment serves as the bottom of that glass tube. The upper end of the tube is open to permit introduction of magnetic beads 3 and the sample 17 that is to be tested for a specific bioagent. A container or reservoir 9, electric valve 10 and conduit 11 are included and form a path from that reservoir into the upper end of glass tube 1. That reservoir contains the supply of the coated magnetic beads 3 in a liquid, such as a water based buffer, forming somewhat of a slurry. When energized, valve 10 allows pumping of a quantity of magnetic beads and the accompanying liquid from the reservoir into the upper end of glass tube 1. Another container or reservoir 13, electric valve 14 and conduit 15 are included and form a path from reservoir 13 into the upper end of glass tube 1. Reservoir 13 contains the sample 17, such as the suspect bioagent, that is to be tested. That sample is in solution (e.g. a sample solution), such as a water based buffer solution. Conduit 15 is positioned so that the axis of the outlet end of the conduit is coaxial with the axis of tube 1, ensuring the sample molecules strike the coated magnetic beads 3 when the sample solution is expressed from the conduit.

Figure 3:
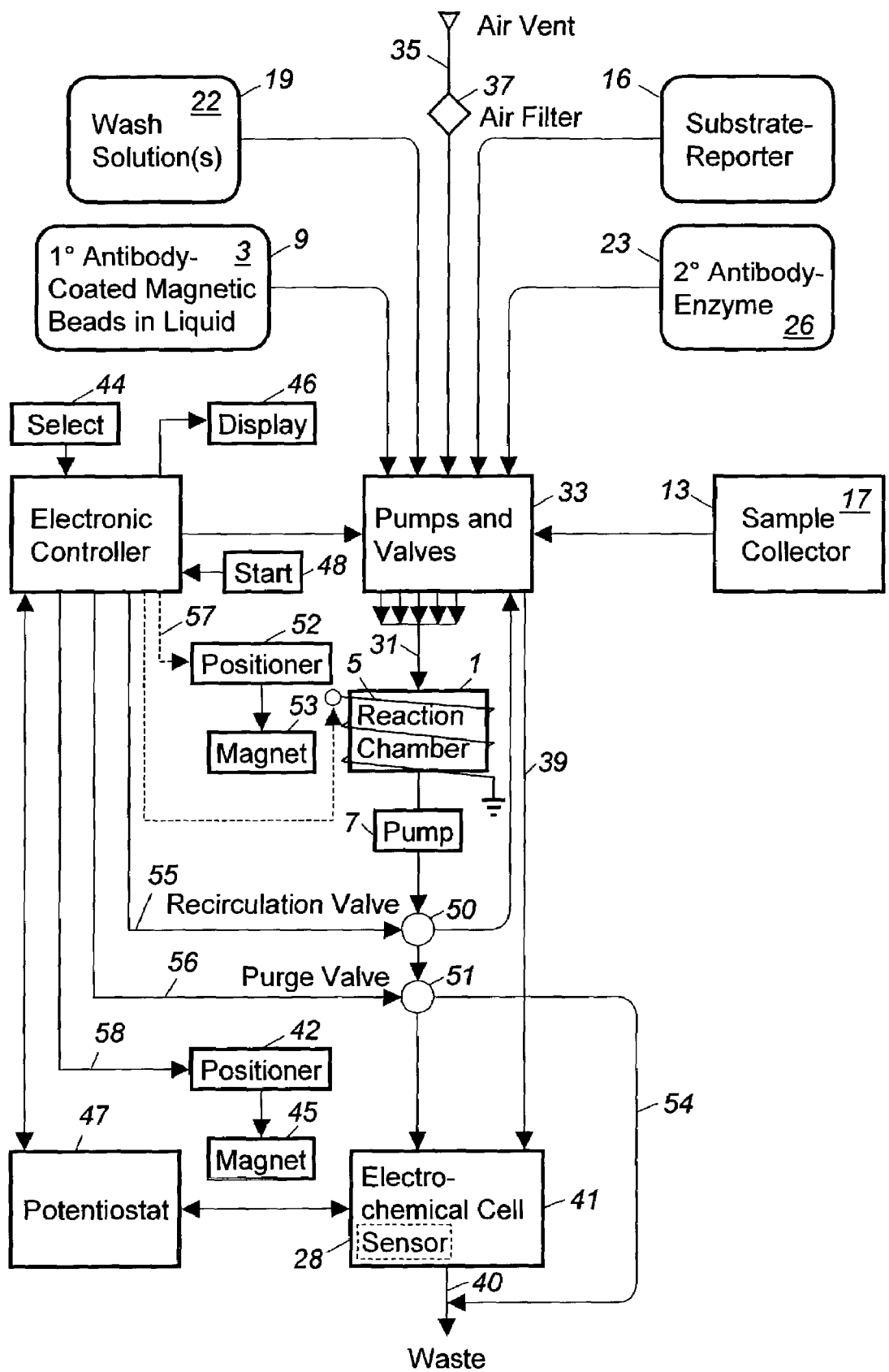
FIG. 3 is a block diagram of an automated ELISA system that incorporates the invention and process of FIGS. 1 and 2.

A third container or reservoir 19, electric valve 20 and conduit 21 are included and provide a path to pump a wash solution 22 into tube 1; and a fourth container or reservoir 23, electric valve 24, and conduit 25 are included to provide a path to pump a 2° antibody enzyme solution 26 into the tube. Reservoirs 19 and 23 and the associated valves and conduits are not necessary to the function of linking the sample molecules to the antibody molecules of the coating on the magnetic beads or to the agglomeration of those coated magnetic beads, but are included in FIG. 1 to assist the reader to place that "mixer" embodiment in context in the improved automated ELISA system embodying such agglomeration system that is illustrated in FIG. 3, later herein described.

In operation, current is applied via lead 27 to valve 10 for a predetermined interval; and a pump, not illustrated, pumps a quantity of the 1° recognition molecule coated magnetic beads 3 through the valve into tube 1. Due to the effect of gravity, the magnetic beads may drift downward in the tube 1 and accumulate in a pile on the bottom (e.g. the closed inlet of pump 7) or, through turbulence of the liquid, may be dispersed in the liquid as a suspension.

By design, DC current, I, is then applied from an external source of power, not illustrated, to the coil and current thereby flows through the coil. The current in the coil produces a static magnetic field B that extends in the vertical direction upward toward the front end of the coil as indicated in the figure (or, alternatively, in the opposite direction, if desired). In an alternate embodiment AC current may be applied to the coil, producing a magnetic field that reverses periodically, but which will have essentially the same effect of the magnetic beads as the static magnetic field. Because the walls of the chamber are of glass, a non-magnetic material, the magnetic flux produced by the current in the coil is able to penetrate the chamber walls. That magnetic field is most intense along the axis of the glass tube, particularly at a location mid-way between the front and rear ends of the coil.

Without application of the magnetic field, the coated magnetic beads may be drifting about in suspension in the solution and/or collecting at a lower location of the tube. The magnetic field agglomerates magnetic beads 3 into an agglomerate, such as depicted in the illustration, that extends along the axis of the tube, producing a porous filter-like structure. Agglomeration is the action of collecting in a mass, and an agglomerate is defined as a collection of elements gathered into a mass or cluster. As long as current flows through the coil, the magnetic beads are pulled and held together as an agglomerate by the magnetic field. Conversely, when the magnetic field is removed, the magnetic beads are no longer bound and may drift apart under the influence of gravity or turbulence of the solution.

Because of the magnetic character of the beads, the beads can be manipulated by a magnetic field. The use of magnetic beads as a carrier for another substance is described in a patent to Glaever, U.S. Pat. No. 4,018,866, granted Apr. 19, 1977. In a practical embodiment of the invention, the magnetic beads are essentially the same size, approximately four and one-half microns in diameter, and are formed of plastic coated iron. Other bead sizes, larger or smaller in diameter, may be substituted if the alternate size beads are found to accomplish the same result or otherwise produce satisfactory result in the test procedure. In lieu of beads other particles can be used if they are capable of being manipulated in the manner described herein.

The current through coil 5 is continued. Valve 14 is then energized via lead 29 and allows a pump, not illustrated, to pump sample solution 17 through conduit 15, expressing the sample solution 17 from the conduit onto the agglomerate of coated magnetic beads 3. In the illustrated embodiment, the expressed sample solution is allowed to percolate (under the influence of gravity) down through the agglomerate or filter-like structure formed by the magnetic beads. In equivalent alternate embodiments of the invention in which the container for the solution of magnetic beads is closed to permit sustaining a positive pressure inside the container, the sample solution may be pumped through the agglomerate of magnetic beads under a positive pressure producing a more forceful flow of sample solution through the agglomerate.

Percolation is generally defined as oozing or trickling through a permeable substance, to seep through the permeable substance. By seeping or flowing down through the agglomerate mass, the sample comes into intimate contact with the coated surface of the beads, ensuring that the molecular portions of the sample links with a respective bead, producing an effective mixing. The effect is to expose the molecules of the sample to as many magnetic beads as possible, so that the molecules of the sample may come into contact with an available coated magnetic bead, a bead that is available to link through the recognition molecule to that sample molecule. The foregoing action emulates the ultimate effect that may be produced by adequately stirring the mixture or by repeatedly pumping the mixture into and out of the tube to produce maximum linkage with the sample molecules.

It is seen that the agglomeration of coated magnetic beads is a filter-like structure on a micro scale, serving to separate sample molecules from the sample solution by allowing the recognition molecule coated magnetic beads to link to and hold onto those sample molecules as the sample solution flows there through.

Once the quantity of sample solution has been dispensed into tube 1, creating the 1° Ab/sample complex on the magnetic beads, the magnetic beads are deemed ready for the next step in the process. The current through coil 5 is then terminated, terminating the magnetic field and releasing the hold on the magnetic beads that then de-agglomerate. The beads may then drift about in the solution or to the bottom of the tube. As one appreciates, the foregoing represents an intermediate stage in the automated ELISA testing process. The bioagent linked antibody coated beads are now ready for further processing. As later herein more fully described, such additional processing includes pumping the wash solution 22 from reservoir 19 and pumping the 2° antibody-enzyme complex 26 from its reservoir. When required by the controller of the automated test system, pump 7 is energized to pump the contents of tube 1 to succeeding stages of the automated ELISA apparatus, later herein discussed in connection with FIG. 3, via conduit 8.

Figure 2:
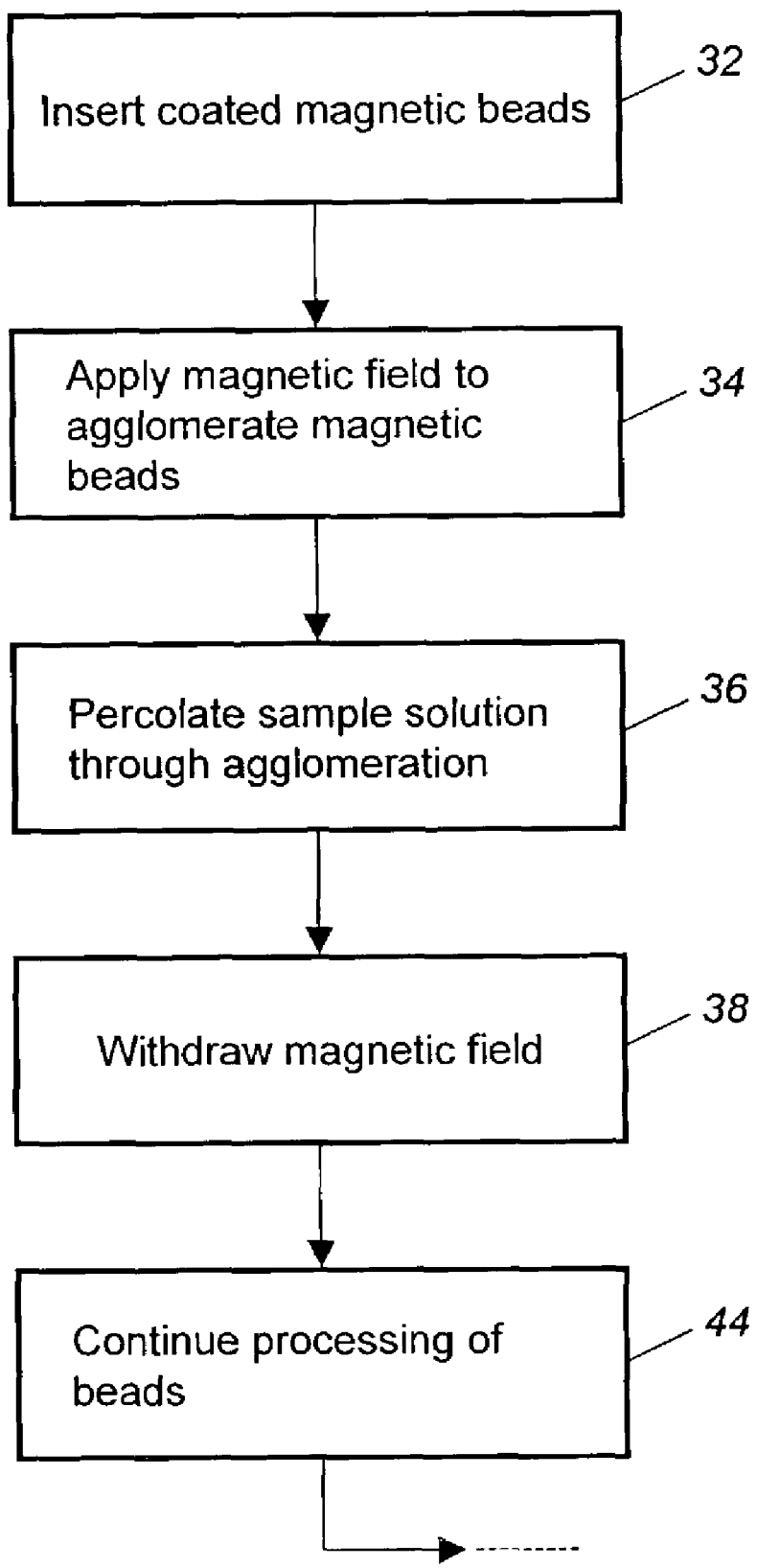
FIG. 2 is a block diagram of the process carried out by the embodiment of FIG. 1.

The foregoing steps (or algorithm) are illustrated more simply in FIG. 2 to which reference is made. First the antibody coated magnetic beads are inserted in the chamber as represented at 32. Then the magnetic field is produced as at 34. The magnetic field extends in the chamber coaxial with the chamber axis to agglomerate the coated magnetic beads. While continuing the magnetic field, the sample solution is percolated or otherwise caused to flow through the agglomerate, as at 36, to mix the sample and the recognition molecule coated beads, producing bioagent/recognition molecule coated beads. The magnetic field is then withdrawn, as represented at 38, de-agglomerating the bioagent/recognition molecule coated magnetic beads. The bioagent/recognition molecule coated magnetic beads are then processed further in accordance with the requirements of the automated system as indicated at 44. The described steps are recognized as a subroutine or algorithm that is carried out by the program of the controller of an automated ELISA system, such as next considered.

Reference is made to FIG. 3, which illustrates a double-stage automated ELISA system in block form. The foregoing system is recognized as the double-stage automated ELISA system described in the prior '946 application that has been modified to incorporate the novel "mixer" apparatus presented in FIGS. 1 and 2. For ease of understanding, the elements that appear in this figure that were earlier identified are identified in this figure by the same number.

The automated apparatus includes the four storage reservoirs or containers 9, 13, 19, and 23, which hold, respectively, the 1° recognition molecule coated magnetic beads 3 in a liquid solution, sample solution 17, the wash solution 22, and the 2° recognition molecule-enzyme solutions 26, earlier described. Reservoir or container 16 holds a substrate reporter solution. Each of the foregoing reservoirs is coupled by the system plumbing to pumps and valves unit 33.

Pump and valve unit 33, illustrated in block form, houses the individual pumps and/or valves, not separately illustrated in the figure, for each of the containers, such as valves 10, 20, 14 and 24 earlier described in connection with FIG. 1. Unit 33 also contains an aspirating pump, not illustrated. As indicated by arrow 31, pump and valve unit 33 is output to the reaction chamber 1. For simplicity of illustration, arrow 31 represents, collectively, the plurality of individual conduits 11, 21, 15 and 25 illustrated in FIG. 1. An electric coil 5 is included, wound around the reaction chamber. The coil may be supported on the outer walls of the chamber.

A fluid conduit 39 extends from the pumps and valves 33 unit into electrochemical cell 41, the container in which the examination of the suspect bioagent is made. Both examination cell 41 and reaction chamber 1 contains walls of non-magnetic material. Waste conduit 40 extends from cell 41 to an appropriate sump or sewer, not illustrated, to permit disposal of the waste of the process.

The apparatus further includes recirculation valve 50 and purge valve 51. Should the program call for recirculating a solution, the controller sets valve 50 to open a path into a circular conduit. For recirculation the aspirating pump is used. Valve 51 is referred to as the purge valve. Instead of commanding that the solution in chamber 1 be pumped into cell 41, the program may instead have the controller set valves 50 and 51 to open a passage into conduit 54 and then initiate an electric pump in unit 33 that pumps the solution in chamber 1 through the valves and out conduit 54. Conduit 54 leads into conduit 40 and leads to the waste disposal system.

An air vent 35 and air filter 37 is plumbed into the pumps unit 33. The air vent and air filter provides a vent to allow air to separate from solutions and/or remove solutions from tubes.

The apparatus includes an electronic controller 43, which is a programmed microprocessor or microcontroller, a magnet positioner 52, suitably a solenoid, and magnet 53 which are employed in connection with the non-magnetic reaction chamber 1, a magnet positioner 42, suitably a solenoid, and a magnet 45 which are employed in connection with the non-magnetic examination cell 41, and a potentiostat 47.

The electronic controller 43 includes selector 44, through which the operator may select the particular antigen (e.g. bioagent) for which the analysis of the sample is being undertaken, a start button 48 and a display 46, such as a liquid crystal display ("LCD"), through which the assay may visually be reported to the operator.

The potentiostat 47 is electrically coupled to a current sensor or, as variously termed, electrochemical reaction sensor 28, represented in dash lines, located inside cell 41. The electrochemical reaction sensor 28 may be any type of sensor that supplies information on the reporter and supplies that information to the electronic controller. One such sensor applies a given voltage across at least two spaced electrodes disposed in the electrochemical cell and senses the level of electric current that flows between those electrodes. However the preferred sensor is of the interdigitated array type one that is described in the cited '16714 PCT application, IPN '870" application and publications cited in the background to this invention. The interdigitated array structure is promulgated as being the most sensitive and, hence, allows better resolution of the data than other known sensors to date in this application.

Magnet 53 is a permanent magnet. The magnet is supported and positioned against the reaction chamber 1, when required, by positioner 52, the latter of which is controlled by controller 43 as indicated by the dash line 57. The positioner is a solenoid actuated electromechanical device that positions the magnet so that the magnetic field produced by the magnet is directed into the reaction chamber or away from that chamber as required by electronic controller 43. Normally, positioner 52 directs the magnetic field of magnet 53 away from the reaction chamber, the default direction. When the positioner receives the command from and is energized by the electronic controller, the positioner moves the permanent magnet into position adjacent the cell so that the permanent magnet directs the magnetic field into the examination cell. When a command is received from controller 43 to extinguish the magnetic field in the reaction chamber 1, the positioner moves the permanent magnet away.

Likewise magnet 45 is a permanent magnet. That magnet is supported and positioned against examination cell 41, when required, by positioner 42, the latter of which is also controlled by controller 43, as indicated in dash lines 58. The positioner is a solenoid actuated electromechanical device that position the magnet so that the magnetic field of the magnet is directed into the examination cell or away from that cell as required by electronic controller 43. Normally, positioner 42 directs the magnetic field of magnet 45 away from the examination cell, the default direction. When the positioner receives the command from and is energized by the electronic controller, the positioner moves the permanent magnet into position adjacent the cell orienting the permanent magnet to direct the magnetic field into the examination cell and through the electrodes of sensor 28 inside that cell. When a command is received from controller 43 to extinguish the magnetic field in examination cell 41, the positioner moves the permanent magnet away.

Potentiostat 47 supplies the voltage to the electrode array, the sensor 28 disposed on the bottom or side of electrochemical cell 41. That is, the sensor carries any extra electrical current that flows in series through the electrode array and potentiostat as a result of the "redox-recycling" reaction that takes place during the latter stage of analysis when the enzyme substrate is cleaved to release the reporter. The potentiostat is also coupled to an input of the controller 43, as represented by dash line 59, and communicates the electrical current levels that flow through the interdigitated array to the controller.

Electronic controller 43 is a programmed microprocessor, microcontroller, computer, as may be variously termed, or the like. The electronic controller controls each of the pumps and valves housed in unit 33 and controls energization of magnet positioners 52 and 42. The controller also enables and receives monitored current readings from potentiostat 47. Controllers of the foregoing type are quite small and may be housed in or embedded in the structure of one of the units, such as in pumps and valves unit 33 so as to be inconspicuous. The foregoing components are packaged into a compact unit that may easily be carried by an individual. For added portability, the controller and pumps may be battery operated. Otherwise, the apparatus may be supplied with electrical operating power from the facility in which used or by a motor generator set.

Electronic controller 43 includes a memory, not separately illustrated, such as ROM or EPROM to permanently store the operating system and the programs as well as temporary memory such as RAM, not separately illustrated. The principal programs of the controller are evident from the description of operation that follows. It will be realized that the controller serves as a sequencing device for controlling the pumps, as a collection point for data, and as a calculating machine for analyzing the data and displaying the result.

For operation, electrical power is connected to electronic controller 43. The operator determines the particular bioagent that is being sought in the sample material, selects the particular bioagent on selector 44, and places the sample 17 in a solution in sample selector container 13. Vessels 9 19, 16 and 23 are filled with the appropriate ingredients, earlier described, for the assay. As thus prepared, the operator operates start button 48, and, in response, electronic controller 43 commences the automatic operation specified in the stored program.

The program of the controller motivates dispensing the contents of container 9, the 1° antibody coated magnetic beads 3 in liquid, commanding the controller to energize the electric valve (10-FIG. 1) associated with that container for a short interval. That valve allows the 1° recognition molecule coated magnetic beads 3 to be pumped into reaction chamber 1. Once in the reaction chamber those magnetic beads accumulate at the bottom of the reaction chamber due to the influence of gravity. The program then commands the controller to supply current to coil 5, which generates a magnetic field that extends coaxially along the axis of the reaction chamber. That magnetic field agglomerates the antibody coated magnetic beads 3.

Maintaining the current into coil 5, the controller then motivates dispensing the contents of sample collector 13 into reaction chamber 1 by commanding the controller to briefly energize the electrical pump, not illustrated, in pumps unit 33 associated with the sample collector container 13. The program then motivates dispensing of the sample into reaction cell 1. As earlier described in connection with FIG. 1, the conduit dispenses the sample solution onto the agglomerate of coated magnetic beads.

The particular recognition molecules that are used to coat the magnetic beads are known to bind to the bioagents of interest or of concern. That is, the recognition molecule coating exhibits a chemical "stickiness" that is selective to specific bioagents. Despite such molecular stickiness, the solution prevents the beads from binding together or forming into clumps. For this description, it is assumed that the sample material is of the suspect bioagent. Hence, the bioagent binds to the coating on the magnetic beads.

Following a short interval the controller program next commands washing of the ingredients in the fluid in reaction chamber 1. For the washing operation, the program commands energization of magnet positioner 52, which moves permanent magnet 53 into position against the chamber to orient a magnetic field inside of the chamber, and commands energization of a pump, not illustrated in the figure, in pumps unit 33, referred to herein as the aspirating pump.

The magnetic field draws the magnetic beads (and the biochemicals bound thereto) to one side of the chamber, vacating the beads from the solution on the other side of the cell. The aspirating pump connects to a conduit that extends into the vacated side of the cell, and the aspirating pump aspirates the fluid and removes the waste fluid. After a suitable interval the program halts the aspirating pump and energizes the valve associated with container 19, which opens. A pump, not illustrated, is also energized, and pumps sufficient clean wash solution 22 through the open valve to replace the liquid that was removed, completing the wash. The solution in the reaction chamber is then agitated to suspend the beads in the solution as by aspirating a small amount of fluid from chamber 1 and then repumping the aspirated fluid back into the vessel often referred to as an "up-down" of the solution. The foregoing washing procedure may be repeated the number of times required by the controller program, and the number written into the program is one that satisfies the requirements of a particular operator's experience. For purposes of this description, the washing step is performed once.

The program then motivates the delivery of the 2° antibody-enzyme into reaction chamber 1 by energizing the pump associated with container 23 for a predetermined interval. The antibody-enzymes then bind to another region of the bioagent, producing a 1° Ab/bioagent/2° Ab-enz complex on the magnetic beads. The operation next proceeds to the reporting stage.

The program next commands controller 43 to open valves 50 and 51 and energize pump 7 to transfer the magnetic beads in solution from reaction chamber 1 into examination cell 41. The program also commands the controller to operate positioner 42 to position magnet 45 to direct the magnetic field into cell 41 and through the sensor 28. The magnetic field produced by magnet 45 draws the magnetic beads 3 and the 1° Ab/bioagent/2° Ab-enz complex carried on the beads toward the sensor 28.

The program of controller 43 next motivates the delivery of the substrate reporter in container 16 into the solution in reaction chamber 1 by commanding energization of an electric pump, not illustrated in the figure, associated with that container. The pump is energized for a predetermined interval and pumps the substrate reporter into the contents within examination cell 41 via conduit 39. Magnet 45 produces a magnetic field that extends through the non-magnetic walls of examination cell 41 and draws the magnetic bead complex to the surface of the test electrodes of electrochemical sensor 28. At that location adjacent the electrode surface of the sensor, the bound enzymes cleave the substrate to produce the reporter molecules. Cleavage of the substrate by the enzyme commences and redox recycling occurs at sensor 28 producing a current through the sensor.

The controller 43 senses the changing electrical current through sensor 28; and potentiostat 47, determines the rate of change of current, i.e. the slope, and, from that slope, determines the concentration of the bioagent. The controller then displays the concentration on the associated LCD display 46, reporting the assay. Upon conclusion of the examination, the contents of the examination cell are discharged through conduit 40 as waste.

Sensor 28 monitors the reaction and reports to the electronic controller 43. In turn, the controller program analyzes the data obtained. To monitor electric current through the examination cell the potentiostat applies a voltage across the spaced interdigitated electrodes, earlier described, which serve as sensor 28. That applied voltage produces an electrical current that passes from one spaced electrode, the anode, through the solution to the other electrode, the cathode. Absent a reaction in the solution, the electric current attains a certain default or base value, depending upon the resistivity of the solution. As the reaction commences to produce the reporter, the resistivity of the solution decreases, increasing the current. The effect is referred to by electrochemists as redox recycling. As the reaction continues producing greater numbers of reporter molecules, the resistivity changes further, as does the electric current. The rate of change of the current is a measure of the concentration of the selected bioagent. Information of the current, whether the information is in digital form or analog form, is coupled to electronic controller 33, which analyzes the changing data in real time.

Essentially concurrently with the pumping of reservoir 16, the controller program commences the checking and assembling of the data on electrical current flow through the sensor by repetitively checking the current readings supplied by potentiostat 47 over a predefined interval of time. For example, one hundred readings may be taken equally spaced over an interval of ten seconds. The data obtained is temporarily stored in the memory of the electronic controller. The program then performs an analysis of the data, as example, a least-squares analysis, and the analysis generates the slope of the sensor current (e.g. change of current level vs. time), a number that represents the rate of change of current.

The electronic controller also stores in memory (ROM or EPROM) a library of the standards that have previously been established in the laboratory to identify bioagents or antigens and the concentration of the respective antigen in a solution by measuring the rate of change of current that occurs when using the known electrochemical ELISA procedure. Each antigen or bioagent produces a rate of change of current that depends on the concentration of the bioagent in the sample. For any given combination of recognition molecule(s) and bioagent or other antigen, a given concentration produces, a unique rate of change of current. The increase in current as a function of time from the beginning of the chemical reaction to produce the reporter is essentially linear, and produces a straight line curve of the type $I=at+b$, where "t" represents time, "b" is an initial constant, a number, and "a" is the slope of the line, also a number. The foregoing slope information and the correlation of that information to respective concentration levels has been tabulated and serves as the standards.

Thus, for each combination of recognition molecule(s) and bioagent or other antigen that is to be studied, the library, often referred to as a "look-up table", contains the correlation between the slope numbers and the concentration levels correlated to those slope numbers. After concluding the regression analysis and obtaining the slope number, the controller program checks to determine which bioagent or antigen was selected by the operator and then accesses the stored look-up table for the selected bioagent or antigen. The computer then compares the slope obtained in the foregoing regression analysis with corresponding slopes obtained in measurements of standard concentrations. Once the computer locates the closest match, the computer then displays the concentration of the antigen on display 46. Optionally, the computer may be programmed to also display the calculated slope. Further, since the volume of the electrochemical cell is known, the computer may also optionally display the total quantity of antigen in the test sample.

As one appreciates, the mixer invention integrates nicely within and improves upon the speed and sensitivity of the automated ELISA system. No additional electric pumps are required for the mixing. The foregoing apparatus is recognized as being automatic in operation, is very "user-friendly" and does not require highly skilled personnel to operate. Incorporated within a compact housing and with optional battery or house supply power the apparatus is portable and suited for use on location. As those skilled in the art appreciate, although the ELISA testing has been described in connection with antibodies and bioagents, the same protocols and processes may also be used to detect proteins and nucleic acids; and the ELISA procedure may in respect of those additional substances be referred to as ELISA-like.

It is believed that the foregoing description of the preferred embodiments of the invention is in sufficient detail to enable one skilled in the art to make and use the invention without undue experimentation. However, it is expressly understood that the detail of the elements comprising the embodiment presented for the foregoing purpose is not intended to limit the scope of the invention in any way, in as much as equivalents to those elements and other modifications thereof, all of which come within the scope of the invention, will become apparent to those skilled in the art upon reading this specification. Thus, the invention is to be broadly construed within the full scope of the appended claims.

What is claimed is:

1. A process to emulate mixing a sample solution with 1° recognition molecule coated magnetic beads, comprising the steps of:

inserting 1° recognition molecule coated magnetic beads into a non-magnetic confinement region when an exit end is closed, said non-magnetic confinement region defined by a non-magnetic cylindrical tube, said non-magnetic cylindrical tube including an entrance end, said exit end and an axis, said cylindrical tube being oriented vertically and said entrance end being positioned vertically above said exit end;

generating a magnetic field coaxial with said axis of said non-magnetic cylindrical tube to agglomerate said 1° recognition molecule coated magnetic beads into a porous mass that fills at least a substantial portion of the cross-section of said cylindrical tube, said step of generating a magnetic field including applying an electric current through a helical path about said axis of said non-magnetic cylindrical tube;

depositing said sample solution onto said porous mass while maintaining said magnetic field and said porous mass in a fixed position to allow said sample solution to seep through said porous mass due to the effect of gravity wherein portions of said sample solution stick to respective 1° recognition molecule coated magnetic beads to form a 1° recognition molecule/sample complex on said beads; and withdrawing said magnetic field to de-agglomerate said 1° recognition molecule coated magnetic beads.

2. The process to emulate mixing a sample solution with 1° recognition molecule coated magnetic beads as defined in claim 1, wherein said step of depositing said sample solution onto said porous mass while maintaining said magnetic field and said porous mass in a fixed position further comprises the step of pumping said sample solution onto said porous mass and allowing said sample solution to seep through said porous mass.

3. The process to emulate mixing a sample solution with 1° recognition molecule coated magnetic beads as defined in claim 1, wherein said step of depositing said sample solution onto said porous mass while maintaining said magnetic field and said porous mass in a fixed position further comprises the step of pumping said sample solution under positive pressure onto said porous mass.

* * * * *